United States Patent [19]
Renga et al.

[11] Patent Number: 5,093,536
[45] Date of Patent: Mar. 3, 1992

[54] PREPARATION OF FUNCTIONALIZED ALKYNES HAVING INTERNAL TRIPLE BONDS

[75] Inventors: James M. Renga; Alan G. Olivero; Mark Bosse, all of Santa Rosa, Calif.

[73] Assignee: Kenkel Research Corporation, Santa Rosa, Calif.

[21] Appl. No.: 433,922

[22] Filed: Nov. 8, 1989

[51] Int. Cl.$^5$ .................... C07C 29/58; C07C 33/042; C07C 43/14; C07C 87/24
[52] U.S. Cl. .................... 568/873; 568/673; 568/692; 564/509
[58] Field of Search .................... 568/873, 692, 673; 564/509

[56] References Cited

U.S. PATENT DOCUMENTS

| 2,448,739 | 9/1948 | Ross | 570/246 |
| 3,028,403 | 4/1962 | Fritz et al. | 570/246 |

FOREIGN PATENT DOCUMENTS

| 6092229 | 7/1981 | Japan | 568/873 |

OTHER PUBLICATIONS

Dehmlow et al., "Tetrahydron", vol. 37 (1981) pp. 1653 to 1658.
Kimura et al., "J. Org. Chem.", vol. 47 (1982), pp. 2493 and 2494.
Gorguer et al., "Tetrahydron Letters", No. 51 (1976), pp. 4723 and 4724.
Just. Lieb. Ann. 1866, 140, pp. 39–75.
Just. Lieb. Ann. 1867, 143, pp. 22–41.
Just. Lieb. Ann. 1867, 143, pp. 41–57.
Just. Lieb. Ann. 1865, 135, pp. 226–229.
J. Org. Chem., 1982, 47, p. 2493.
Tetrahedron Letters No. 51, pp. 4723–4724, 1976.
Tetrahedron Letters No. 37, pp. 1653–1658, 1981.

Primary Examiner—J. E. Evans
Attorney, Agent, or Firm—Ernest G. Szoke; Wayne C. Jaeschke; John E. Drach

[57] ABSTRACT

Functional internal alkynes are conveniently and economically prepared by dehydrohalogenating a dibromide with an alkali metal hydroxide in the presence of a phase transfer catalyst.

11 Claims, No Drawings

PREPARATION OF FUNCTIONALIZED ALKYNES HAVING INTERNAL TRIPLE BONDS

BACKGROUND OF THE INVENTION

1. Field of the Invention

This invention relates to a process for preparing functionalized alkynes having internal triple bonds.

2. Description of the Related Art

The preparation of acetylenic compounds by bromination followed by dehydrobromination is known in the art. Fatty alkynes such as stearolic acid, palmitolic acid, behenolic acid, and ricinstearolic acid have been prepared from the corresponding olefinic fatty acids by bromination and dehydrohalogenation with alcoholic potassium hydroxide (Ann., 1866, 140, 39; Ann., 1867, 143, 27; Ann., 1867, 143, 41; Ann., 1865, 135, 226). Aqueous potassium and sodium hydroxides have also been used along with a polyethylene glycol catalyst in the dehydrohalogenation of internal vicinal dibromohydrocarbons to acetylenic hydrocarbons. (J. Org. Chem., 47, 2493, 1982). Aqueous sodium hydroxide has similarly been used in the presence of tetrabutyl ammonium bisulfate to eliminate vicinal dibromo-hydrocarbons to acetylenic hydrocarbons (Tetrahedron Letters, 1976, 4723). Solid potassium hydroxide in the presence of phase transfer catalysts such as quaternary amines (Aliquat 336, tetraoctyl ammonium bromide) or crown ethers (18-crown-6) has been used to accomplish the dehydrohalogenation of vicinal dibromo hydrocarbons (Tetrahedron, 1981, 37, 1653). None of the prior art methods provides a process for preparing alkynes that uses an inexpensive base such as potassium or sodium hydroxide in the solid state in the presence of polyethylene glycols to produce alkynes. None of the prior art methods provides a process for preparing alkynes that utilizes solid sodium hydroxide in the presence of a phase transfer catalyst for dehydrohalogenation to yield an alkyne product that is easily separated from the reaction mixture.

SUMMARY OF THE INVENTION

The present invention provides an inexpensive and convenient process for the preparation of a functional alkyne having an internal triple bond which employs a solid alkali metal hydroxide as the base used for dehydrohalogenation and provides for the easy isolation of the reaction product from the reaction mixture. The process comprises (1) substantially completely brominating a functional internal olefin to form a dibromo compound; (2) contacting said dibromo compound with a liquid phase transfer catalyst and solid alkali metal hydroxide for a time period sufficient to form a reaction mixture comprising a liquid phase containing said alkyne and said phase transfer catalyst and a solid phase comprising an alkali metal bromide and said alkali metal hydroxide; (3) separating said solid phase from said liquid phase; and (4) isolating said alkyne.

DESCRIPTION OF THE PREFERRED EMBODIMENTS

The present invention provides a process for the preparation of a functional internal alkyne which employs a solid alkali metal hydroxide in the presence of a phase transfer catalyst and provides for the easy isolation of the reaction product from the reaction mixture.

A functional internal alkyne is a compound of the formula 1

wherein at least one of $R^1$ and $R^2$ is a linear or branched alkyl group having from 1 to 19 carbons such that the total number of carbon atoms in the molecule is from about 7 to about 22 and having one or more —OH, —NH$_2$, —NHR$^3$, —NR$^3_2$, or —OR$^3$ groups wherein R$^3$ is linear or branched alkyl group having from 1 to 19 carbon atoms and one of $R^1$ or $R^2$ is a linear or branched alkyl group having from 1 to 19 carbons such that the total number of carbon atoms in the molecule is from about 7 to about 22. Examples of such functional internal alkynes include but are not limited to 9-octadecyn-1-ol, 1-amino-9-octadecyne, 1-methoxy-9-octadecyne, di-(9-octadecynyl) ether.

Any functional internal olefin having at least one —OH, —NH$_2$, —NHR$^3$—NR$^3_2$ or —OR$^3$ functionality that is a liquid at about 140° C. may be used in the process of the present invention. A functional internal olefin is an olefinically unsaturated compound wherein the double bond is in other than a terminal position and having —OH, —NH$_2$, —NHR$^3$, —NR$^3_2$, or —OR functionalities substituted on carbon atoms other than the olefinic carbon atoms. Examples of such functional alkenes having an internal double bond that are liquid at room temperature include alkenes having a total of from 7 carbon atoms to about 22 carbon atoms include but are not limited to oleyl alcohol, oleyl amine, and methyl oleyl ether.

The process of the present invention is particularly suited for the preparation of fatty functional internal alkynes since the olefinically unsaturated compounds from which they are made are relatively inexpensive and the alkyne product forms a readily separable oily layer in the reaction product mixture. Olefinically unsaturated compounds that are particularly preferred as starting materials are fatty alcohols such as undecylenyl alcohol, myristoleyl alcohol, palmitoleyl alcohol, and oleyl alcohol.

The bromination step of the process of the present invention can be carried out by adding approximately a stoichiometric amount of bromine (based on the total amount of unsaturation in the olefinically unsaturated compound) neat or in a solvent at room temperature. The bromination step substantially completely brominates the alkene which means that greater than about 99% of the alkene is brominated as can be noted by the appearance of a yellow-red color of unreacted bromine upon the addition of a slight excess of bromine. It is preferred that the bromination step be carried out in the absence of solvent (neat).

The dehydrohalogenation step can be carried out by contacting the dibromo compound formed in the bromination step with a solid alkali metal hydroxide such as potassium hydroxide or sodium hydroxide in the presence of a phase transfer catalyst. The preferred alkali metal hydroxide is sodium hydroxide. It is preferred that the sodium hydroxide be used as a finely divided powder. The amount of alkali metal hydroxide that can be used is from about 1.5 to about 10 moles per mole of dibromo compound. The preferred amount is from about 2 to about 5 moles per mole of dibromo compound.

The phase transfer catalysts that are suitable for use in the process of the present invention are liquid quaternary ammonium salts and polyethylene glycols. The preferred liquid quaternary ammonium salts are fatty quaternary ammonium compounds such as Aliquat 336 (tricaprylyl methyl ammonium chloride, a product of Henkel Corp).

The preferred phase transfer catalysts are polyethylene glycols. Polyethylene glycols (PEG) which can be used in the process of the present invention are those which have an average molecular weight of from 300 Daltons to 600 Daltons with polyethylene glycol 300 (PEG 300) being particularly preferred. The preferred amount of phase transfer catalyst is from about 0.1 to about 20 weight percent relative to the feed.

The dehydrohalogenation step can be continued until at least 65% of the dibromo compound has been converted to alkyne as determined by analysis of the reaction mixture preferably by gas chromatography. In order to realize a reaction mixture containing at least 65% by weight of alkyne product, the reaction mixture may have to be heated to a temperature of from about 80° C. to about 150° C., preferably 20° C. to about 150° C., for a period of time sufficient to convert the vinyl bromide intermediate to alkyne product as determined by analysis of the reaction mixture preferably by gas chromatography.

An advantage associated with the process of the present invention lies in the fact that since the process is carried out using solid alkali metal hydroxide and in the absence of reaction solvent, the isolation of the alkyne product is very simple.

After the dehydrohalogenation step has been completed, the reaction mixture is allowed to cool to room temperature whereupon a solid and a liquid phase separate from each other. The solid phase is composed of a sodium bromide formed in the reaction and the unreacted solid sodium hydroxide while the liquid phase contains the phase transfer catalyst and the alkyne product. The method of isolating the alkyne product depends upon the solubility of the alkyne product in the phase transfer catalyst. If the alkyne product is not soluble in the phase transfer catalyst, then the alkyne product is isolated by phase separation. If it is soluble in the phase transfer catalyst, the alkyne product is isolated by distillation.

In a preferred embodiment of the process of the present invention, approximately a stoichiometric amount of bromine is added to a neat functional internal olefin until a yellow color persists. After the bromination step, about 5% to about 10% by weight of PEG 300, is added to the reaction mixture along with about 2.5 equivalents (relative to moles of olefin) of powdered sodium hydroxide. The resulting reaction mixture is then heated to about 120° C. to 150° C. and maintained there for about 2 to 5 hours with vigorous stirring. The reaction mixture is then cooled to room temperature and the solid phase comprising sodium bromide formed in the reaction and the unreacted solid sodium hydroxide is then separated from the liquid phase by filtration. The alkyne product is isolated from the liquid phase, which contains the PEG 300 and the alkyne product, either by phase separation or by distillation to give about an 80% yield of product.

The following examples are meant to illustrate but not limit the invention.

EXAMPLE 1

Preparation of 9-Octadecyn-1-ol from Oleyl Alcohol

Oleyl alcohol (9.80 g, 36.5 mmoles, Sigma) was placed in a 25 ml 3-neck roundbottom flask equipped with a thermometer, an overhead mechanical stirrer, and a reflux condenser. The contents of the flask were cooled to 15° C. and bromine (5.83 g, 36.5 mmole) was added slowly with stirring at such a rate as to keep the reaction temperature below 30° C. After addition of the bromine, the reaction was stirred at room temperature for 10 minutes. Polyethylene glycol 300 (1.0 g, Fluka) was added followed by powdered sodium hydroxide (3.65 g, 91.3 mmoles). A large exotherm was noted which brought the reaction temperature to 150° C. The reaction was stirred vigorously with heating to maintain a temperature of 125° C. for 2.5 hours. The reaction was cooled and filtered to remove the solid sodium bromide. The filtered salts were washed with 25 ml of hexanes and the solvent removed. The crude product was kugelrohr distilled (ca. 200° C./0.20 torr) to yield 9-octadecyn-1-ol (7.89 g, 81% yield) as a clear colorless liquid which solidified upon standing. $^1$H NMR (CDCl$_3$): 3.61 (q, 2H), 2.12 (m, 4H), 1.02–1.87 (m, 25H), 0.88 (t, 3H) $^{13}$C NMR(CDCl$_3$): 79.94, 79.84, 62.33, 32.48, 31.65, 29.19, 29.04, 28.96, 28.66, 28.61, 25.58, 22.45, 18.52, 13.84.

IR (thin film): 3320, 2920, 2840, 1460, 1440, 1050.

MP: 33°–35° C. (uncorrected).

GC: 97%; C, H, Analysis: C: 81.72, H: 12.99

EXAMPLE 2

Preparation of 6-Octadecyn-1-ol from Petroselinyl Alcohol

Petroselinyl alcohol (0.66 g, 2.46 mmoles, Sigma) was placed in a 10 ml 3-neck roundbottom flask equipped with a reflux condenser. Bromine (0.40 g, 2.5 mmole) was added slowly with magnetic stirring. After addition of the bromine, polyethylene glycol 300 (60 mg, Fluka) was added followed by powdered sodium hydroxide (0.250 g, 6.25 mmoles). A large exotherm was noted. The reaction was stirred vigorously with heating to maintain a temperature of 125° C. for 2.5 hours. The reaction was cooled and filtered to remove the solid sodium bromide. The filtered salts were washed with 25 ml of hexanes and the solvent removed. The crude product was kugelrohr distilled (ca. 200° C./0.20 torr) to yield 6-octadecyn-1-ol (0.49 g, 75% yield) as a clear colorless liquid which solidified upon standing.

$^1$H NMR (CDCl$_3$) 3.60 (m, 2H), 2.12 (m, 4H), 1.054–1.86 (m, 25 H), 0.88 (t, 3H).

$^{13}$C NMR(CDCl$_3$): 80.38, 79.77, 62.66, 32.18, 31.84, 29.56, 29.49, 29.28, 29.09, 28.83, 24.91, 22.61, 19.65, 14.02.

IR (thin film): 3310, 2920, 2840, 1460, 1050.

GC: 95% weight percent

EXAMPLE 3

Preparation of 11-Hexadecyn-1-ol from cis-11-Hexadecen-1-ol

Cis-11-Hexadecen-1-ol (4.94 g, 20.4 mmoles, Sigma) was placed in a 25 ml 3-neck roundbottom flask equipped with a thermometer, an overhead mechanical stirrer, and a reflux condenser. The contents of the flask were cooled to 15° C. and bromine (3.28 g, 20.4 mmole) was added slowly with stirring at such a rate as to keep the reaction temperature below 30° C. After addition of the bromine, the reaction was stirred at room temperature for 10 minutes. Polyethylene glycol 300 (0.5 g, Fluka) was added followed by powdered sodium hydroxide (2.05 g, 51.25 mmoles). A large exotherm was noted which brought the reaction temperature to 150° C. The reaction was stirred vigorously with heating to maintain a temperature of 125° C. for 2.5 hours. The reaction was cooled and filtered to remove the solid sodium bromide. The filtered salts were washed with 25 ml of hexanes and the solvent removed in vacuo. The crude product was kugelrohr distilled (ca. 160° C./0.20 torr) to yield 11-hexadecyn-1-ol (3.88 g, 80% yield) as a clear colorless liquid.

$^1$H NMR (CDCl$_3$): 3.67 (m) 2.45 (m), 1.03-1.68 (m)

$^{13}$C NMR(CDCl$_3$): 79.91, 79.88, 62.38, 32.50, 31.06, 29.40, 29.28, 28.96, 28.64, 25.61, 21.70, 18. 52, 18.21, 13.38.

IR (thin film): 3300, 2910, 2820, 1460, 1150

GC: 89% weight percent

EXAMPLE 4

Preparation of 9-Octadecyn-1-ol from Technical Oleyl Alcohol

Technical oleyl alcohol (40.0 g, 150 mmoles, Ocenol 90/95, Henkel KGaA) was placed in a 250 ml 3-neck Morton flask equipped with a thermometer, an overhead mechanical stirrer, and a reflux condenser. The contents of the flask were cooled to 15° C. and bromine (24.0 g, 150 mmole) was added slowly with stirring at such a rate as to keep the reaction temperature below 30° C. After addition of the bromine, the reaction was stirred at room temperature for 10 minutes. Polyethylene glycol 300 (4.0 g, Fluka) was added followed by powdered sodium hydroxide (15.0 g, 375 mmoles). A large exotherm was noted which brought the reaction temperature to 150° C. The reaction was stirred vigorously with heating to maintain a temperature of 125° C. for 2.5 hours. The reaction was cooled and filtered to remove the solid sodium bromide. The filtered salts were washed with 100 ml of hexanes and the solvent removed. The crude product was kugelrohr distilled (ca. 200° C./0.20 torr) to yield a clear colorless liquid (30.7 g) which was determined by gas chromatography to be 51% by weight 9-octadecyn-1-ol.

EXAMPLE 5

Preparation of 9-Octadecyn-1-ol from Technical Oleyl Alcohol Using Potassium Hydroxide Technical oleyl alcohol (40.0 g, 150 mmoles, Ocenol 90/95, Henkel KGaA) was placed in a 250 ml 3-neck Morton flask equipped with a thermometer, an overhead mechanical stirrer, and a reflux condenser. The contents of the flask were cooled to 15° C. and bromine (24.0 g, 150 mmole) was added slowly with stirring at such a rate as to keep the reaction temperature below 30° C. After addition of the bromine, the reaction was stirred at room temperature for 10 minutes. Polyethylene glycol 300 (4.0 g, Fluka) was added followed by powdered potassium hydroxide (24.7 g of 85%, 375 mmoles). A large exotherm was noted which brought the reaction temperature to 135° C. The reaction was stirred vigorously with heating to maintain a temperature of 125° C. for 2.5 hours. The reaction was cooled and filtered to remove the solid potassium bromide. The filtered salts were washed with 100 ml of hexanes and the solvent removed in vacuo. The crude product was kugelrohr distilled (ca. 200° C. 0.20 torr) to yield a clear colorless liquid (28.4 g) which was determined by gas chromatography to be 58% by weight 9-octadecyn-1-ol.

EXAMPLE 6

Gas Chromatographic Conditions

Samples were silylated with trimethylsilylchloride for 45 minutes at 70° C. Pentadecanol was used as an internal standard. Column 23 meter×0.32 mm I.D. capillary fused silica, DB-5 stationary phase. Injection temperature-290° C.; column temperature program of 3 min at 100° C., rising at 12° C./min to 320° C., and holding for 6 min. ECN (effective carbon number) response factors were used for 11-hexadecyn-1-ol and 6- and 16-octadecyn-1- ol.

What is claimed is:

1. A process for preparing an alkyne of the formula I

$$R^1-C\equiv C-R^2 \qquad I$$

wherein at least one of R$^1$ and R$^2$ is a linear or branched alkyl group having from 1 to 19 carbons such that the total number of carbon atoms in the molecule is from about 7 to about 22 and having one or more —OH, —NH$_2$, —NHR$^3$, —NR$^3$$_2$, or —OR$^3$ groups wherein R$^3$ is linear or branched alkyl group having from 1 to 19 carbon atoms and one of R$^1$ or R$^2$ is a linear or branched alkyl group having from 1 to 19 carbons such that the total number of carbon atoms in the molecule is from about 7 to about 22 comprising the steps of: (1) substantially completely brominating a functional internal olefin to form a dibromo compound; (2) contacting said dibromo compound with a polyethylene glycol having a molecular weight of from about 300 daltons to about 600 daltons and solid alkali metal hydroxide for a time period sufficient to form a reaction mixture comprising a liquid phase containing said functional alkyne and a solid phase comprising an alkali metal bromide and said alkali metal hydroxide; and (3) separating said solid phase from said liquid phase; and (4) isolating said functional alkyne.

2. The process of claim 1 wherein said step (2) is carried out at a temperature of from about 80° C. to about 150° C.

3. The process of claim 2 wherein said step (2) is carried out at a temperature of from about 120° C. to about 150° C.

4. The process of claim 1 wherein the molecular weight of said polyethylene glycol is about 300 daltons.

5. The process of claim 1 wherein said polyethylene glycol is present in an amount of from about 0.1% to about 20% by weight.

6. The process of claim 5 wherein said polyethylene glycol is present in an amount of from about 2.0% to about 10% by weight.

7. The process of claim 1 wherein said alkali metal hydroxide is potassium hydroxide or sodium hydroxide.

8. The process of claim 7 wherein said alkali metal hydroxide is sodium hydroxide.

9. The process of claim 8 wherein said sodium hydroxide is present in an amount of from about 1.5 to about 10 moles per mole of dibromo compound.

10. The process of claim 9 wherein said sodium hydroxide is present in an amount of from about 2.0 to about 5.0 moles per mole of dibromo compound.

11. The process of claim 1 wherein in step (4) said functional alkyne is isolated by distillation.

* * * * *

UNITED STATES PATENT AND TRADEMARK OFFICE
CERTIFICATE OF CORRECTION

PATENT NO. : 5,093,536

DATED : March 03, 1992

INVENTOR(S) : James M. Renga et al.

It is certified that error appears in the above-identified patent and that said Letters Patent is hereby corrected as shown below:

On the title page item [73], Assignee:

--Henkel Research Corporation, Santa Rosa, Calif.--

Signed and Sealed this

Third Day of August, 1993

Attest:

MICHAEL K. KIRK

Attesting Officer

Acting Commissioner of Patents and Trademarks